(12) United States Patent  
Becker et al.

(10) Patent No.: US 11,998,475 B2
(45) Date of Patent: Jun. 4, 2024

(54) MALE URINARY INCONTINENCE DEVICE

(71) Applicant: Coloplast A/S, Humlebaek (DK)

(72) Inventors: Kim Becker, Hilleroed (DK);
Kristoffer Zeuthen, Copenhagen (DK);
Marie Bay Borg, Broenshoej (DK)

(73) Assignee: Coloplast A/S, Humlebaek (DK)

( * ) Notice: Subject to any disclaimer, the term of this patent is extended or adjusted under 35 U.S.C. 154(b) by 639 days.

(21) Appl. No.: 17/053,360

(22) PCT Filed: May 7, 2019

(86) PCT No.: PCT/DK2019/050139
§ 371 (c)(1),
(2) Date: Nov. 6, 2020

(87) PCT Pub. No.: WO2019/214787
PCT Pub. Date: Nov. 14, 2019

(65) Prior Publication Data
US 2021/0228401 A1    Jul. 29, 2021

(30) Foreign Application Priority Data
May 7, 2018    (DK) ............................ PA 2018 70276

(51) Int. Cl.
*A61F 5/453*    (2006.01)
*A61F 5/44*    (2006.01)

(52) U.S. Cl.
CPC ............ *A61F 5/453* (2013.01); *A61F 5/4401* (2013.01); *A61F 5/4407* (2013.01)

(58) Field of Classification Search
CPC ...... A61F 5/4401; A61F 5/4408; A61F 5/443; A61F 5/442; A61F 5/441; A61F 5/44;
(Continued)

(56) References Cited

U.S. PATENT DOCUMENTS 4,588,397 A * 5/1986 Giacalone ............... A61F 5/453
604/351
4,650,817 A * 3/1987 Allen, Jr. ............ C08G 18/4081
428/317.1
(Continued)

FOREIGN PATENT DOCUMENTS

DE    4236130 A1    5/1993
FR    2881045 A1    7/2006
(Continued)

*Primary Examiner* — Benjamin J Klein
*Assistant Examiner* — Gabriella E Burnette
(74) *Attorney, Agent, or Firm* — Coloplast Corp., Coloplast A/S; Nick Baumann

(57) ABSTRACT

A male urinary incontinence device comprising a top end portion, a bottom end portion and an intermediate portion for containing at least a part of a penis, the top end portion comprising an inlet through which the penis can be entered, the inlet being provided with a cuff member. The cuff member comprises a membrane provided with a through-going aperture, and a first collar provided around the aperture, the first collar extending axially away from a first surface of the membrane, and a second collar provided around the aperture, the second collar extending axially away from a second surface of the membrane. The membrane and the first and the second collar are configured to allow elastic expansion of the aperture to fittingly engage with the penis.

16 Claims, 5 Drawing Sheets

(58) Field of Classification Search
CPC ............... A61F 5/453; A61F 2006/044; A61F 2006/045; A61F 2006/047; A61F 2006/041; A61F 6/02; A61F 6/04; A61B 10/007
See application file for complete search history.

(56) References Cited

U.S. PATENT DOCUMENTS

| | | | | |
|---|---|---|---|---|
| 5,300,052 | A | * | 4/1994 | Kubo ..................... A61F 5/453 604/350 |
| 5,361,947 | A | * | 11/1994 | Lifshey .................. B65D 47/10 206/532 |
| 5,409,475 | A | | 4/1995 | Steer |
| 5,478,334 | A | * | 12/1995 | Bernstein ............... A61F 5/448 604/353 |
| 6,209,142 | B1 | * | 4/2001 | Mattsson ................ A61F 5/453 2/403 |
| 2002/0177825 | A1 | | 11/2002 | Scovel |
| 2004/0034335 | A1 | | 2/2004 | Dolan |
| 2005/0177133 | A1 | | 8/2005 | Nielsen et al. |
| 2008/0243097 | A1 | * | 10/2008 | Goss ..................... A61F 5/453 604/349 |

FOREIGN PATENT DOCUMENTS

| | | | |
|---|---|---|---|
| WO | 06077351 A1 | 7/2006 | |
| WO | WO-2006077351 A1 * | 7/2006 | ............. A61F 5/453 |

* cited by examiner

MALE URINARY INCONTINENCE DEVICE

The invention relates to a male urinary incontinence device.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
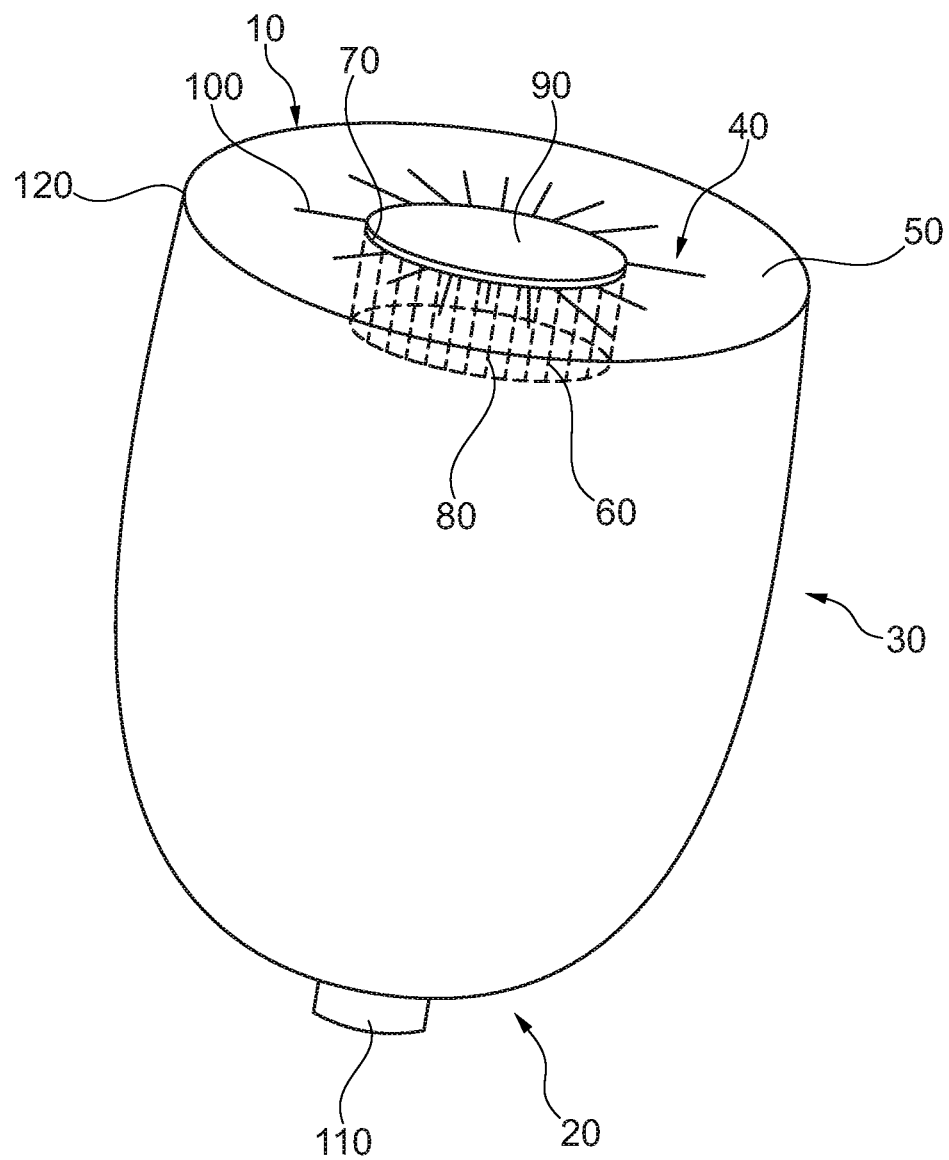
FIG. 1 is an isometric view of one embodiment of a male urinary incontinence device.

Embodiments, and features of the various exemplary embodiments described in this application, may be combined with each other ("mixed and matched"), unless specifically noted otherwise.

In the following Detailed Description reference is made to the accompanying drawings, which form a part hereof, and in which is shown by way of illustration specific embodiments in which the invention may be practiced. Because components of embodiments can be positioned in different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Throughout this disclosure, the words "patient" or "user" are used to address the person to wear the male urinary incontinence device. However, in some cases "user" may also relate or refer to a health care professional (HCP), such as a surgeon or continence care nurse or others. In those cases, it will either be explicitly stated, or be implicit from the context that the "user" is not the "patient" himself.

In the following, whenever referring to a proximal side of a device or part of a device, the proximal side is the side closest to the user, when the device is fitted on a user and the distal side is the opposite side—the side furthest away from the user in use.

The axial direction is defined as the direction of the penis, when the device is worn by a user. The radial direction is defined as transverse to the axial direction that is transversely to the direction of the penis. Thus, the radial direction is substantially perpendicular to the penis of the user. The longitudinal direction is the direction from the proximal top portion to the distal bottom portion. The transverse direction is the direction perpendicular to the longitudinal direction, which corresponds to the direction across the intermediate portion.

The use of the phrase "substantially" as a qualifier of certain features or effects throughout this disclosure is intended to simply mean that any deviations are within tolerances that would normally be expected by the skilled person in the relevant field.

Many people suffer from light incontinence. Stress incontinence means that you leak urine when you sneeze, cough, laugh, lift something, change position, or do something that puts stress or strain on your bladder. Urge incontinence is an urge to urinate that is so strong that you cannot make it to the toilet in time. It also happens when your bladder squeezes when it shouldn't. This can happen even when you have only a small amount of urine in your bladder. Overactive bladder is a kind of urge incontinence. Where the amount of leaked urine in stress incontinence may be quite small such as few drops, the amount of leaked urine in urge incontinence may be larger, such as up to 180 ml a day.

Male urinary incontinence aiding systems are known. Widely used systems known as external urinary catheters and urisheaths normally comprise a roll-on sheath or body portion for enclosing the shaft of the penis, and a tip portion that is provided with a comparatively short discharge tube, which via a tube is connected to a urine collection bag that is fastened to the leg of the user. The sheath portion is rolled-up in a number of successive windings to such an extent that adhesive on the inner surface of the sheath is accommodated in the windings. However, unrolling of a sheath correctly on a penis can be very challenging and it is essential that the sheath is fitted correctly to ensure a good sealing between the skin of the penis and the sheath. The known systems are especially intended and designed for persons suffering from medium to high urine incontinence, and the urine collection bags having a capacity of 500 ml are rather big and inconvenient to wear.

There is a need for a lightweight and discreet male urinary incontinence device that may conveniently be sealingly arranged on the penis and having a smaller capacity of about 100-300 ml and be more agreeable for the user to wear in case of lighter incontinence.

Incontinent users and health care professionals alike would welcome improvements in continence care devices to better meet such requirements.

Embodiments relate to a male urinary incontinence device comprising a top end portion, a bottom end portion, and an intermediate portion for containing at least a part of a penis, the top end portion comprising an inlet through which the penis can be entered, the inlet comprising a cuff member comprising a membrane with a through-going aperture, and a first collar provided around the aperture, the first collar extending axially away from a first surface of the membrane, and a second collar provided around the aperture, the second collar extending axially away from a second surface of the membrane, wherein the membrane and the first collar and the second collar are configured to allow elastic expansion of the aperture to fittingly engage with the penis. Thus, the first collar is extending in opposite direction of the second collar.

In embodiments, the first collar is extending substantially perpendicular to and axially away from a first surface of the membrane. In embodiments, the second collar is extending substantially perpendicular to and axially away from a second surface of the membrane. In embodiments, the first collar defines an angle with the membrane of 45-120 degrees. The angle between the first collar and the membrane may be defined by the anatomy of the body but easy manufacturing of the cuff member may also be considered while choosing the angle.

In embodiments, the device is provided with an outlet at the bottom end portion. Such outlet may be connected, optionally via a tube or hose, to urine collecting means. In embodiments, the collecting means comprises a collecting bag. The outlet may be recloseable or it may be provided with a single use seal to be broken before use. In embodiments, the pocket may be closed at the bottom end portion. In embodiments, the device comprises an absorbent element configured to absorb urine.

In embodiments, the bottom end portion and the intermediate portion together defines a pocket. In embodiments, the pocket may comprise an absorbent element. The absorbent element is configured to absorb urine leaking from the penis. In embodiments, the absorbent element may be an integrated part of the device. This may be a suitable solution for a single use device. In embodiments, the absorbent element is a discrete element that can be exchanged and replaced with a fresh element without changing the whole device. In embodiments, the absorbent element may be provided with a handle for easy exchange of the absorbent element. Absorbent materials suitable for an absorbent element may comprise any absorbent material that is capable of absorbing and retaining fluids such as urine.

In embodiments, at least the bottom end portion is provided with a liquid barrier layer. In embodiments, the pocket is provided with a liquid barrier layer. The liquid barrier layer may comprise water impermeable material. In embodiments, the pocket comprises a water impermeable film layer. In embodiments, the liquid barrier layer is in the form of a coating. In embodiments, the pocket is splash-proof. In embodiments, the device is provided with a cover layer, such as a textile or non-woven to provide a pleasant surface towards the skin of the user as well as facilitate a nice appearance. In embodiments, the cover layer is on the outside surface of the device.

In embodiments, at least a part of the inside surface of the device is provided with a skin-friendly surface, such as a non-woven. Such skin-friendly surface may provide comfort for the user as well as it may have moisture-transporting properties, securing a dry surface against the skin.

The cuff member provides a sufficient sealing against the shaft of the penis and enables easy application of the device. In embodiments, the cuff member is water impermeable. In embodiments, the cuff member is water impermeable but moisture permeable. In embodiments, the cuff member is splash proof.

In embodiments, the cuff serves to provide a splash proof fit to the penis. The first and the second collar of the cuff may seal against the shaft of the penis, with a pressure sufficiently high as to provide at least a splash proof sealing, but not so high that it may cause discomfort for the user.

In embodiments, the cuff member comprises a flexible material such as an elastomer. In embodiments, the cuff member comprises a silicone material. In embodiments, the cuff member, comprising the membrane, the first collar, and second collar is made in the same material. The material of the cuff member may be soft, flexible and elastic. In embodiments, the cuff member comprises a thermoplastic elastomer. The elasticity of the cuff member may allow that the same cuff member can be fitted to a wide range of penis sizes as both the first collar and the second collar and the membrane is designed to allow expansion of the through-going aperture. By flexible/elastic is herein meant that the material is able to stretch to fit around penises of different sizes.

From a manufacturing point of view thermoplastic elastomers are often preferred to thermoset elastomers as they inter alia can be formed by injection moulding.

In embodiments, the first collar, the second collar and/or the membrane—or the entire cuff member of the device can be made from a thermoset elastomer, such as natural rubber latex, nitrile rubber latex, chloroprene rubber latex, SBS rubber latex or other synthetic lattices or from silicone or polyurethane dispersions or emulsions.

In embodiments, the length of the first collar is longer than the length of the second collar. The height of the collar is measured in axial direction from the membrane. The length of the first collar is chosen to be long enough to provide at least a splash proof fit to the penis and short enough to be comfortable for the user. In embodiments, the first collar has a length between 5-30 mm, such as 8-25 mm such as 10-20 mm or even between 12-18 mm.

In embodiments, the presence of the first collar facilitates better sealing and pressure distribution by detaching the pressure from the pocket. Furthermore, the first collar may decrease the risk of achieving pressure marks.

In embodiments, the cuff member is not necessarily able to hold the device in place. The device may be secured to the body by the underwear/pants of the user.

In embodiments, the second collar and the first collar may together define a tubular structure, being substantially perpendicular to the membrane. The tubular structure may be of substantially equal diameter over the entire length. The second collar is shorter than the first collar.

In embodiments, the length of the second collar is shorter than the length of the first collar. In embodiments, the length of the second collar is 0.6-2.0 mm, such as 0.8-1.5 mm such as 0.9-1.4 mm or even 1.0-1.3 mm. In embodiments, the first collar is at least 10 times as long as the second collar.

In embodiments, the thickness of the second collar is the same as the thickness of the first collar. The first collar may have a thickness of 0.2-0.6 mm, such as 0.3-0.5 mm such as about 0.4 mm. The thickness of the collars is measured in radial direction. In embodiments, the thickness of the second collar is thicker than the thickness of the first collar. The enhanced thickness, compared to the first collar, provides more stability of the device and renders it less prone to roll or invert during application. In embodiments, the second collar has a thickness being less than the thickness of the first collar.

In embodiments, the cuff member is oriented with the first collar facing the inside of the device. In embodiments, the cuff member is oriented with the first collar facing the outside (facing the body of the user) of the device. The collar facing the body of the user may facilitate that the cuff member does not roll away as well as it provides sealing against the penis.

In embodiments, the first collar is provided with ribs extending in axial direction. In embodiments, the ribs may be in the form of areas of increased thickness of the first collar. In embodiments, the ribs may be in the form of pleated areas. The ribs serve to avoid rolling of the first collar during application to the penis, providing a structure stiffer in axial direction.

In embodiments, the through-going aperture is substantially circular or oval. In embodiments, the diameter of the aperture, measured in radial direction, is 18-40 mm, such as 19-35 mm, such as 20-32 mm.

In embodiments, the membrane is a sheet-like elastic layer. In embodiments, the membrane has a thickness of 0.2-0.8 mm, such as 0.3-0.5 mm. In embodiments, the membrane is substantially circular or oval. The aperture may be located centrally in the membrane or it may have a decentral position. In embodiments, the membrane has a diameter (measured at the broadest point if not circular) of 50-100 mm, such as 60-90 mm, such as 70-85 mm. In embodiments, the diameter of the membrane is at least twice the diameter of the through-going aperture.

In embodiments, the membrane comprises reinforcing members extending from the first collar and radially outwards. The reinforcing members support the structure and stability of the membrane and prevent the membrane from unintended folding and adhesion to itself.

The reinforcing members may be in form of lines of increased thickness of the membrane. The reinforcing members may extend radially from the aperture and at least partly to the outer periphery of the membrane. In embodiments, the reinforcing members may be straight or curvilinear, but substantially in radial direction.

In embodiments, the cuff member may be provided with a plurality of radial support wings extending from an outside surface of the first and/or the second collar and outwards in axial direction towards the to the membrane. Hence, the support wings are attached to both the first collar and the membrane and define a radially extending and substantially triangular structure. These support wings serve to stabilize the construction of the cuff member and may prevent that the first collar or second collar is inverted or may roll during application and use.

In embodiments, the first collar and/or the second collar may be provided with a release liner for storage before use, the liner has a configuration that prevents the collar from collapsing and adhering to itself during storage. The cuff member, including collars and membrane may be self-adhering like cling film.

In embodiments, the device comprises a proximal wall and a distal wall, sealed together along the periphery to form a closed pocket. In embodiments, the cuff member is located in the proximal wall. In embodiments, the proximal wall and the distal wall together defines a hollow body and the cuff member defines the top end portion. In embodiments, the membrane constitutes at least a part of the proximal wall of the device. In embodiments, the membrane constitutes the entire proximal wall of the device.

Embodiments relate to a male urinary incontinence device comprising a proximal wall and a distal wall, the proximal wall comprising an aperture for receiving a penis therethrough, the distal wall and the proximal wall combining to define a top section and a bottom section of the device, wherein an edge portion of the proximal wall and an edge portion of the distal wall at the bottom section of the device are sealed together to form a pocket, and wherein the proximal wall and the distal wall at the top section of the device combine to define an openable door configured to be sealingly shut to close the door in a liquid-tight/splash-proof manner. Thus, when the door is closed, the device defines a closed enclosure for the penis.

In embodiments, the distal wall may be provided with slit, extending at least partly from one side edge to another side edge of the distal wall. The slit may serve as a door for accessing the inside of the device. The slit may be formed by having an upper section of the distal wall to be at least partly overlying a lower section of the distal wall. The overlapping portion of the distal wall may be provided with means for closing the slit. In embodiments such closing means can be adhesive or Velcro. The slit facilitates the user to insert his hand through the slit and pull the penis through the aperture of the cuff member. When the penis is arranged in the pocket of the device, the slit can be closed. In embodiments, the closing means are splash-proof or even waterproof.

By splash-proof is herein meant that a sample is tested to be rated to (at least) grade 3 on the Ingress Protection (IP) scale. The IP scale for moisture is shown in Table 1 below.

In embodiments, when the user is urinating (spray or splash) while wearing the device (in closed conformation), the top end portion of the device, including the door and the cuff member, should seal sufficiently enough to keep the urine inside the device. This can be tested by the below shown IPx3 scale, where water is sprayed onto the product in a 60 degree angle from vertical. During the test, water should not pass to the other side of the cuff member and the closed door in order to fulfil the IPx3 rating. When referring to "splash-proof" herein, is meant a resistance to moisture ingress rating at least 3 on the IP scale.

In embodiments, the top end portion of the device is resistant to moisture ingress by rating at least 4 on the IP scale.

In embodiments, the bottom end portion may show the same resistance to moisture ingress as the top end portion, being at least 3 on the IP scale. In embodiments, the bottom end portion is waterproof. This is tested by filling the device with water up to the cuff member (the device is held in upright position with top end portion at top). During the test, the device should not leak water.

TABLE 1

| IP scale, second digit: Ingress of liquids | |
|---|---|
| 0 | No protection. |
| 1 | Protected against vertically falling drops of water or condensation. |
| 2 | Protected against falling drops of water, if the case is disposed up to 15 from vertical. |
| 3 | Protected against sprays of water from any direction, even if the case is disposed up to 60 from vertical. |
| 4 | Protected against splash water from any direction. |
| 5 | Protected against low pressure water jets from any direction. Limited ingress permitted. |
| 6 | Protected against short periods of immersion in water. |
| 7 | Protected against long, durable periods of immersion in water. |
| 8 | Protected against close-range high pressure, high temperature spray downs. |

Embodiments relate to a kit of parts comprising a cuff member comprising a membrane provided with a through-going aperture, and a first collar provided around the aperture, the first collar extending substantially perpendicular to and axially away from a first surface of the membrane, and a second collar provided around the aperture, the second collar extending substantially perpendicular to and axially away from a second surface of the membrane, wherein the membrane and the first and the second collar are configured to allow elastic expansion of the aperture to fittingly engage with the penis, and a device comprising a top end portion, a bottom end portion and an intermediate portion for containing at least a part of a penis.

DETAILED DESCRIPTION OF THE DRAWING

Embodiments, and features of the various exemplary embodiments described in this application, may be combined with each other ("mixed and matched"), unless specifically noted otherwise.

FIG. 1 shows a device with a top end portion 10 a bottom end portion 20 and an intermediate portion 30 connecting the top end portion 10 and the bottom end portion 20. At the bottom end portion 20 may be provided an outlet 110 that may be used for leading urine from the device to a collecting bag, e.g. via a tube (not shown). The intermediate portion 30 is in the form of a hollow body extending from the top end portion 10 to the bottom end portion 20 and is configured to accommodating at least a length of a penis or at least the tip of a penis. The bottom end portion 20 and the intermediate portion 30 defines a pocket being open at the top end portion. At the top end portion 10 is provided a cuff member 40. The cuff member 40 comprises a membrane 50 with a through-going aperture 90 and a first collar 60 and a second collar 70 provided around said aperture 90. The first collar 60 is facing the inside of the device and is therefore partly shown in dotted lines in the Figure. The first collar 60 is extending in axial direction away from the first surface of the membrane 50. The second collar 70 is extending in axial direction away from the second surface of the membrane 50. The first collar 60 may be provided with ribs 80 in the form of axially extending lines of enhanced thickness of the first collar 60. At the membrane 50, radially extending from the aperture, are a plurality of reinforcing members 100. The reinforcing members 100 may extend from the aperture 90 and the entire way towards the periphery 120 of the membrane, or the reinforcing members 100 may extend partly from the aperture 90 towards the periphery 120 of the membrane.

Figure 2:
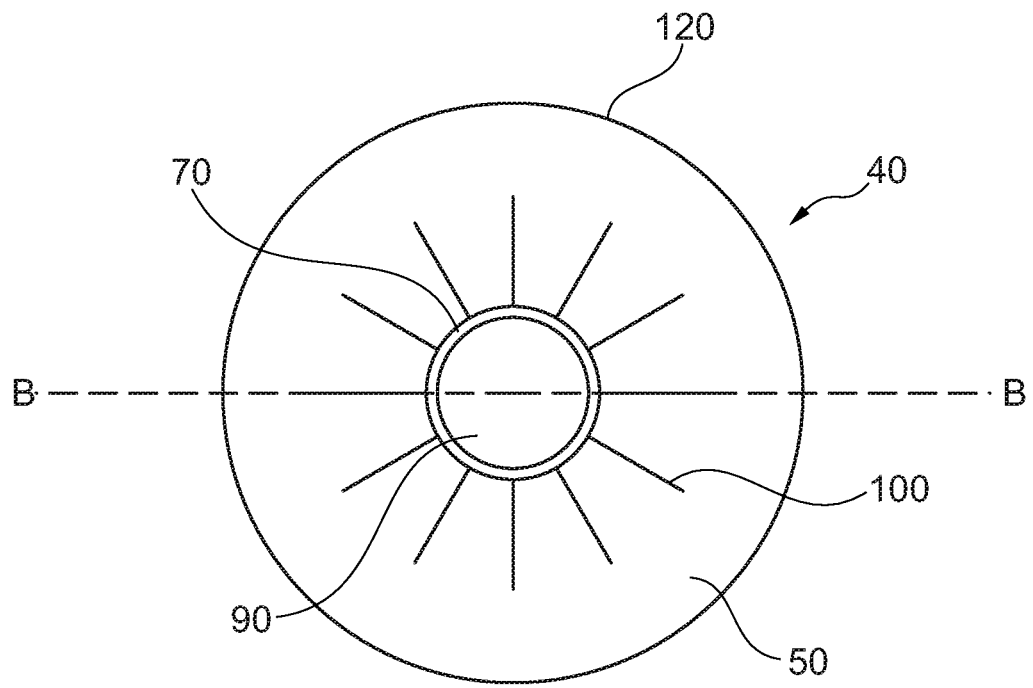
FIG. 2 is a top view of an embodiment of a cuff member of a male urinary incontinence device.

In FIG. 2 is shown an embodiment of a cuff member 40 seen from the proximal side. The pocket is omitted from the drawing for clarity.

Figure 3:
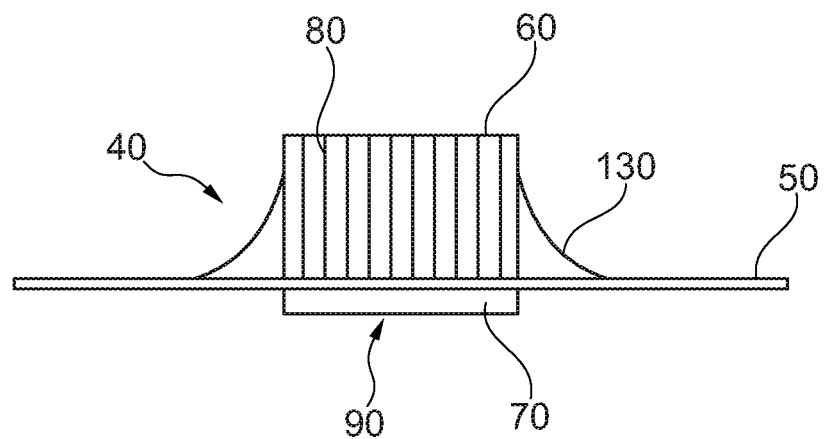
FIG. 3 is a cross-sectional view of the embodiment shown in FIG. 2, cut along the B-B line.
Figure 4:
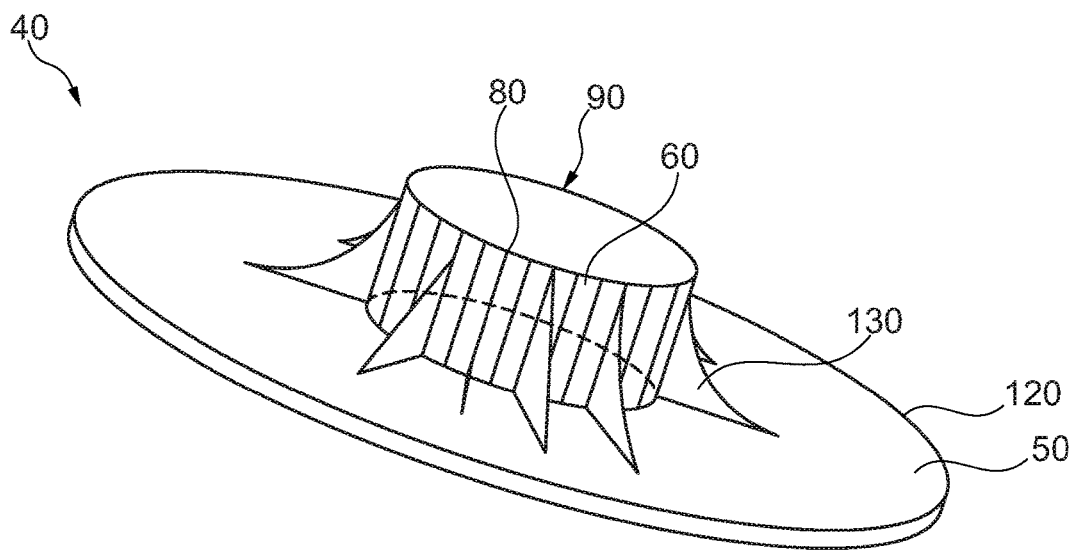
FIG. 4 is an isometric view of the cuff member shown in FIG. 2.

FIG. 3 is showing a cross-section along the B-B line of the cuff member 40 of FIG. 2. In FIG. 4, the cuff member 40 is shown in perspective. The cuff member 40 comprises a membrane 50 with a through-going aperture 90 and a first collar 60 and a second collar 70 provided around said aperture 90. The first collar 60 is extending in axial direction from the first surface of the membrane 50 and the second collar 70 is extending in axial direction from the second surface of the membrane 50. The first collar 60 is longer than the second collar 70. The first collar 60 may be provided with ribs 80 in the form of axially extending lines of enhanced thickness of the first collar 60. The membrane may be provided with reinforcing members 100 extending in radial direction from the aperture 90. The first collar 60 is provided with supporting wings 130 on the outside surface, the supporting wings 130 extending radially and being connected to the membrane 50. The supporting wings 130 may constitute a part of the ribs 80 of the first collar 60 and/or the reinforcing member 100 of the membrane 50 such that these structures 130,100,80 appear as a single unit.

Figure 5:
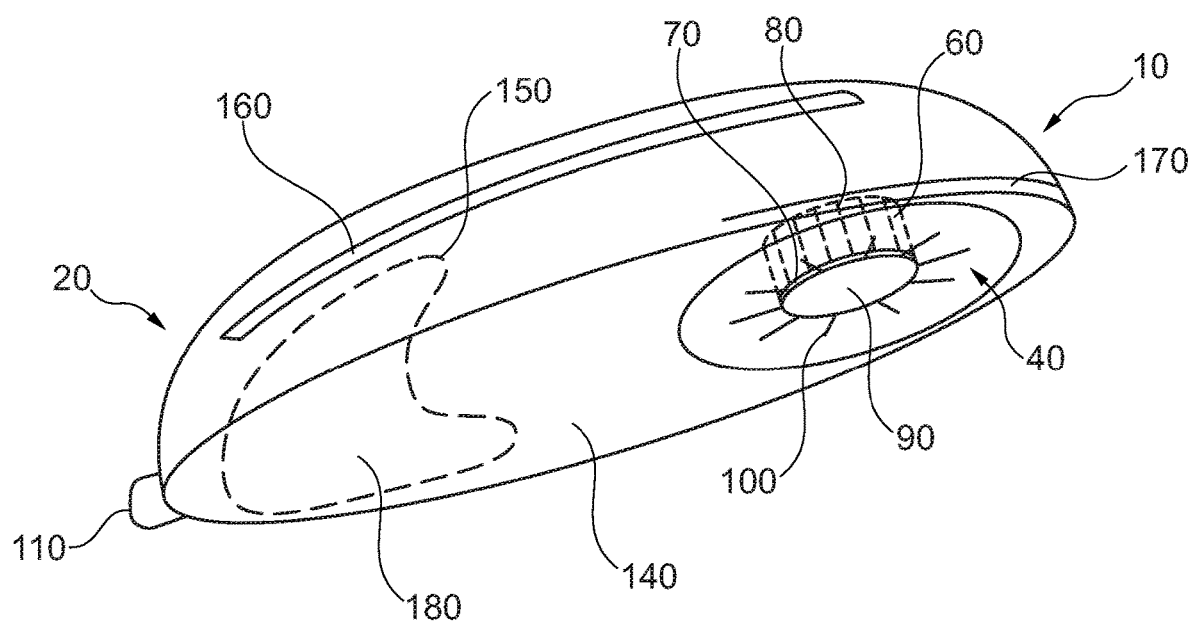
FIG. 5 is an isometric view of an embodiment of the male urinary incontinence device.

In FIG. 5 is shown an embodiment of a male urinary incontinence device 10. In this embodiment, the device comprises a proximal wall 140 and a distal wall 150, the proximal wall 140 and the distal wall 150 being sealed along the edge portion to constitute a closed pocket. The pocket has a bottom end portion 20, optionally comprising an outlet 110, and a top end portion 10 comprising a cuff member 40. The cuff member 40 is located in the proximal wall 140. In the distal wall 20 is provided one or more pleats 160 allowing the distal wall 150 to expand into a three-dimensional shape, thereby providing room for accommodating at least a length of a penis. In the top end portion 10 of the device, the sealing of the periphery of the proximal wall 140 and the second end portion 150 may be openable to define a closure 170. During application of the device, the closure 170 is opened, the penis is pulled through the aperture of the cuff member 40 and the closure 170 is closed again. The pocket may be equipped with an absorbent pad 180. The absorbent pad can be exchanged through the closure 170.

Figure 6:
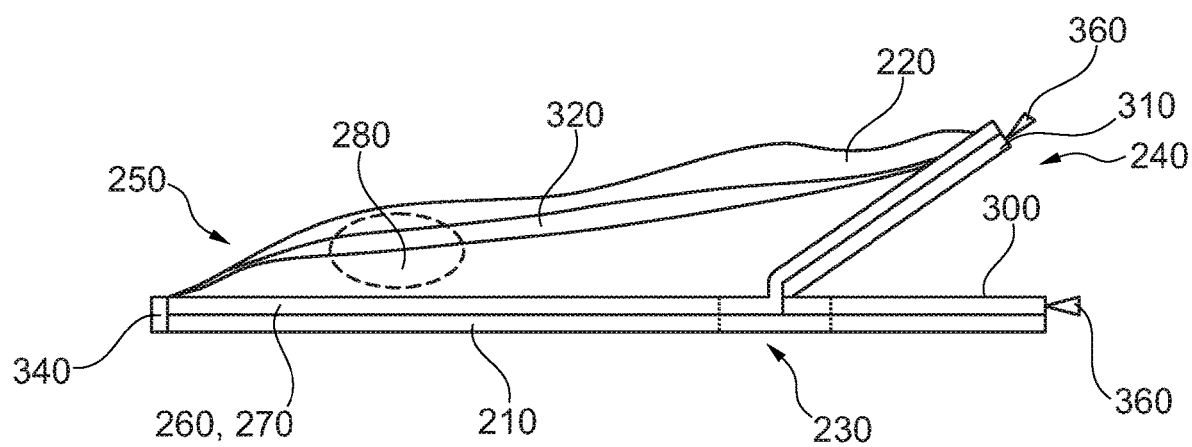
FIG. 6 is a cross-sectional view of an embodiment shown in open configuration.

In FIG. 6 is shown a male urinary incontinence device in open configuration. The device comprises a proximal wall 210 and a distal wall 220. The distal wall 220 and the proximal wall 210 are combined to define a top portion 240 and a bottom end portion 250 of the device, wherein an edge portion 260 of the proximal wall and an edge portion 270 of the distal wall at the bottom end portion 250 of the device are sealed together to form a pocket 280. At the top portion 240 of the device, the proximal wall 210 and the distal wall 220 combine to define an openable door 290 configured to be sealingly shut to close the door 290 in an at least splash-proof manner. The door 290 comprises a first lip portion 300 on the proximal wall 210 and a second lip portion 310 and the distal wall 220. When the lip portions 300,310 are brought into contact with each other, the door 290 is closed and when the lip portions 300,310 are separated from each other, the door 290 is open. The first lip portion 300 may comprise an adhesive layer. The second lip portion 310 may comprise a release layer enabling the adhesive of the first lip portion 300 to fasten to it and easily release from it again when the door 290 is opened and closed. The lip portions 300,310 defines a part of a circle, such as a half-circle. The door 290 is provided with tab members 360 for facilitating easy opening of the door 290. The tab members 360 may be arranged on the edge portion of the top end portion 240 of the device, on the distal wall 220 and the proximal wall 210. When the door 290 is closed, the tabs 360 may be displaced apart from each other, facilitating easy separation of the tabs 360. The tabs 360 may be a part of the lip portions 300,310, extending radially away from the device. The tabs 360 may be configured to interact with each other to form a lock when the door 290 is in closed position. In embodiments, tabs 360 are provided with Velcro or adhesive in order lock the door 290 in closed position. The distal wall 220 may be provided with pleats 320 in longitudinal direction. The pleats 320 facilitate that the device can expand in volume to provide room for a penis and optionally an absorbent element 330. When not in use, the device may have a substantially two-dimensional (flat) configuration. In the bottom end portion 250 of the device is optionally provided an outlet 340. In the proximal wall 210 of the device is provided an aperture 230 for receiving a penis therethrough. A cuff member 350 is surrounding the aperture 230, the cuff member 350 being flexible and elastic and configured to provide sealing against the penis. The aperture 230 is located in the top end portion 240 of the proximal wall 210.

Figure 7:
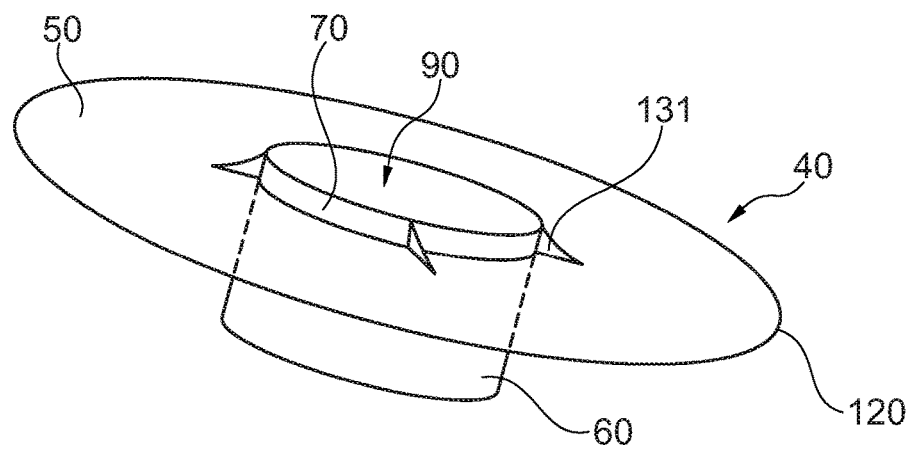
FIG. 7 is a perspective view of an embodiment of a cuff member of male urinary incontinence device.

In FIG. 7 is shown an embodiment of a cuff member 40 in perspective. The cuff member 40 comprises a membrane 50 with a through-going aperture 90 and a first collar 60 and a second collar 70 provided around said aperture 90. The first collar 60 is extending in axial direction from the first surface of the membrane 50 and the second collar 70 is extending in axial direction from the second surface of the membrane 50. The first collar 60 is longer than the second collar 70. The second collar 70 is provided with supporting wings 131 on the outside surface, the supporting wings 131 extending radially and being connected to the membrane 50.

Figures 8, 9:
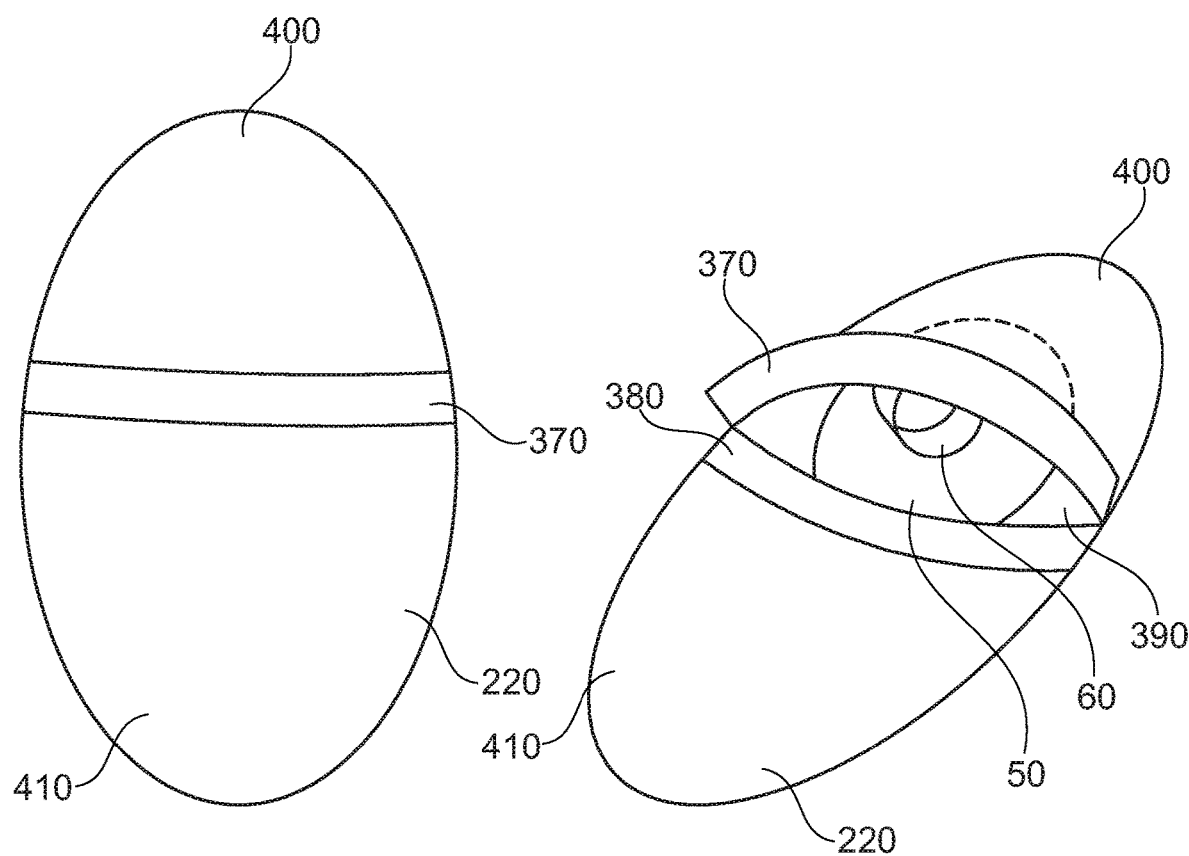
FIG. 8 is a distal view of an embodiment of a male urinary incontinence device.
FIG. 9 is a perspective view of the male urinary incontinence device shown in FIG. 8.

In FIG. 8 and FIG. 9 are shown an embodiment of a male urinary incontinence device seen from the distal side and in perspective, facing the distal wall 220. Across the distal wall 220, extending at least partly from one side edge to another side edge, is provided a slit 390 for accessing the inside of the device. The slit 390 is formed by an upper section 400 of the distal wall overlying at least partly a lower section of the distal wall 410. The overlapping portion 370 of the distal wall may be provided with means for closing the slit 390, such as adhesive or Velcro. The slit facilitates the user to enter his hand through the slit 390 and pull the penis through the aperture 90 of the cuff member 40 when applying the device to the user. When the penis is arranged in the pocket of the device, the slit 390 can be closed. The pocket of the device may be provided with absorbent means to control any flow of urine (not shown).

The invention claimed is:

1. A male urinary incontinence device comprising:
    a top end portion, and a pocket connected to the top end portion, where the pocket is formed by an intermediate portion extending between the top end portion and a bottom end portion, and the pocket is configured to contain at least a part of a penis; and
    a cuff member coupled to the top end portion, where the cuff member comprises a membrane with an aperture adapted to receive the at least the part of the penis, a first collar provided around the aperture, with the first collar extending axially away from a first surface of the membrane in a distal direction inside of and into the pocket, and a second collar provided around the aperture, with the second collar extending axially away from a second surface of the membrane in a proximal direction outside of and away from the pocket;
    wherein the membrane and the first collar and the second collar are configured to allow elastic expansion of the aperture to fittingly engage with the at least the part of the penis;
    wherein the second collar and the first collar together define a tubular structure that is substantially perpendicular to the membrane, with the tubular structure having a substantially equal diameter over an entire length of the tubular structure;
    wherein the membrane is provided with radially extending reinforcing members extending from the first collar and directed radially outwards.

2. The device according to claim 1, wherein a length of the first collar is longer than a length of the second collar.

3. The device according to claim 1, wherein the first collar is provided with axially extending ribs.

4. The device according to claim 1, wherein the cuff member comprises a plurality of radially extending wings on an outside surface of the first collar that extend from the first collar to attach to the membrane.

5. The device according to claim 1, wherein the cuff member comprises a plurality of radially extending wings on an outside surface of the second collar that extend from the second collar to attach to the membrane.

6. The device according to claim 1, wherein the first collar and the second collar and the membrane are made from the same material.

7. The device according to claim 1, wherein the cuff member comprises a thermoplastic elastomer.

8. The device according to claim 1, wherein the pocket is a closed pocket comprising a proximal wall and a distal wall sealed together along the periphery and at the bottom end portion.

9. The device according to claim 1, wherein the bottom end portion comprises an outlet.

10. The device according to claim 1, wherein the device comprises absorbent material.

11. The device according to claim 1, wherein the membrane provides an entirety of a proximal wall of the device, with the aperture formed in the proximal wall of the device and the first collar extends away from the proximal wall in the distal direction and the second collar extends away from the proximal wall opposite of the first collar and in the proximal direction.

12. The device according to claim 1, wherein the first collar and the second collar are elastic and adapted to stretch to fit around differently sized penises.

13. The device according to claim 1, wherein a distal wall of the device is formed by the intermediate portion extending between the top end portion and the bottom end portion, the device further comprising a slit formed in the distal wall, with the slit is adapted to be opened to allow movement of the penis through the slit and out of the pocket.

14. The device according to claim 1, wherein the bottom end portion comprises an outlet configured as a single use outlet having a seal to be broken before use.

15. A male urinary incontinence device comprising:
    a top end portion, and a pocket connected to the top end portion, where the pocket is formed by an intermediate portion extending between the top end portion and a bottom end portion, and the pocket is configured to contain at least a part of a penis; and
    a cuff member coupled to the top end portion, where the cuff member comprises a membrane with an aperture adapted to receive the at least the part of the penis, a first collar provided around the aperture, with the first collar extending axially away from a first surface of the membrane in a distal direction inside of and into the pocket, and a second collar provided around the aperture, with the second collar extending axially away from a second surface of the membrane in a proximal direction outside of and away from the pocket;
    wherein the membrane and the first collar and the second collar are configured to allow elastic expansion of the aperture to fittingly engage with the at least the part of the penis;
    wherein the second collar and the first collar together define a tubular structure that is substantially perpendicular to the membrane, with the tubular structure having a substantially equal diameter over an entire length of the tubular structure;
    wherein the cuff member comprises a plurality of radially extending wings on an outside surface of the first collar that extend from the first collar to attach to the membrane.

16. A male urinary incontinence device comprising:
    a top end portion, and a pocket connected to the top end portion, where the pocket is formed by an intermediate portion extending between the top end portion and a bottom end portion, and the pocket is configured to contain at least a part of a penis; and
    a cuff member coupled to the top end portion, where the cuff member comprises a membrane with an aperture adapted to receive the at least the part of the penis, a first collar provided around the aperture, with the first collar extending axially away from a first surface of the membrane in a distal direction inside of and into the pocket, and a second collar provided around the aperture, with the second collar extending axially away from a second surface of the membrane in a proximal direction outside of and away from the pocket;
wherein the membrane and the first collar and the second collar are configured to allow elastic expansion of the aperture to fittingly engage with the at least the part of the penis;
wherein the second collar and the first collar together define a tubular structure that is substantially perpendicular to the membrane, with the tubular structure having a substantially equal diameter over an entire length of the tubular structure;
wherein the cuff member comprises a plurality of radially extending wings on an outside surface of the second collar that extend from the second collar to attach to the membrane.

* * * * *